United States Patent
Lefcort et al.

(10) Patent No.: US 10,702,514 B2
(45) Date of Patent: Jul. 7, 2020

(54) USE OF BGP15 TO TREAT FAMILIAL DYSAUTONOMIA

(71) Applicants: MONTANA STATE UNIVERSITY, Bozeman, MT (US); N-GENE RESEARCH LABORATORIES, INC., New York, NY (US)

(72) Inventors: Frances Brenda Lefcort, Bozeman, MT (US); Michael Jay Brownstein, Rockville, MD (US)

(73) Assignees: N-GENE RESEARCH LABORATORIES, INC., New York, NY (US); MONTANA STATE UNIVERSITY, Bozeman, MT (US)

( * ) Notice: Subject to any disclaimer, the term of this patent is extended or adjusted under 35 U.S.C. 154(b) by 0 days.

(21) Appl. No.: 15/637,257

(22) Filed: Jun. 29, 2017

(65) Prior Publication Data

US 2018/0000809 A1    Jan. 4, 2018

(30) Foreign Application Priority Data

Jul. 1, 2016 (EP) .................................... 16177516

(51) Int. Cl.
*A61K 31/4545* (2006.01)

(52) U.S. Cl.
CPC .................. *A61K 31/4545* (2013.01)

(58) Field of Classification Search
None
See application file for complete search history.

(56) References Cited

U.S. PATENT DOCUMENTS

2006/0069045 A1    3/2006   Rubin et al.

OTHER PUBLICATIONS

Palma et al, "Current Treatments in Familial Dysautonomia", Expert Opin. Pharmacother., 2014, vol. 15, No. 18, pp. 2653-2671.*
"Familial Dysautonomia", ClinicalTrials.gov, accessed Sep. 14, 2017.*
G. Bárdos, et al., BGP-15, a hydroximic acid derivative, protects against cisplatinor taxol-induced peripheral neuropathy in rats, Toxicology and Applied Pharmacology, 2003, pp. 9-16, vol. 190, Elsevier Science.
Gábor Nagy, et al., BGP-15 inhibits caspase-independent programmed cell death in acetaminophen-induced liver injury, Toxicology and Applied Pharmacology, 2010, pp. 96-103, vol. 243, Elsevier Inc.
Ramon Clèries, et al., BootstRatio: A web-based statistical analysis of fold-change in qPCR and RT-qPCR data using resampling methods, Computers in Biology and Medicine, 2012, pp. 438-445, vol. 42, Elsevier Ltd.
Jason T. Rifkin, et al., Dynamic Expression of Neurotrophin Receptors during Sensory Neuron Genesis and Differentiation, Developmental Biology, 2000, pp. 465-480, vol. 227, Academic Press.

(Continued)

*Primary Examiner* — James D. Anderson
*Assistant Examiner* — Stephanie K Springer
(74) *Attorney, Agent, or Firm* — Young & Thompson (57) ABSTRACT

Disclosed is the use of O-(3-piperidino-2-hydroxy-1-propyl)-nicotinic amidoxime (BGP15), its tautomers, enantiomers and pharmaceutically acceptable salts thereof for the treatment of Familial Dysaustonomia.

1 Claim, 13 Drawing Sheets

(56) References Cited

OTHER PUBLICATIONS

Ruben K. Dagda, et al., Loss of PINK1 Function Promotes Mitophagy through Effects on Oxidative Stress and Mitochondrial Fission, The Journal of Biological Chemistry, May 15, 2009, pp. 13843-13855, vol. 284, No. 20.

Akiko Enomoto, et al., High Sensitivity of Nrf2 Knockout Mice to Acetaminophen Hepatotoxicity Associated with Decreased Expression of ARE-Regulated Drug Metabolizing Enzymes and Antioxidant Genes, Toxicological Sciences, 2001, pp. 169-177, vol. 59.

Sylvia L. Anderson, et al., Familial Dysautonomia Is Caused by Mutations of the IKAP Gene, American Journal of Human Genetics, 2001, pp. 753-758, vol. 68.

Nicola A. Hawkes, et al., Purification and Characterization of the Human Elongator Complex, The Journal of Biological Chemistry, Jan. 25, 2002, pp. 3047-3052, vol. 277, No. 4.

Tony Karlsborn, et al., Elongator, a conserved complex required for wobble uridine modifications in Eukaryotes, RNA Biology, Dec. 2014, pp. 1519-1528, vol. 11, Issue 12.

Botond Literáti-Nagy, et al., Improvement of Insulin Sensitivity by a Novel Drug Candidate, BGP-15, in Different Animal Studies, Metabolic Syndrome and Related Disorders, 2014, pp. 125-131, vol. 12, No. 2.

Stefan M. Gehrig, et al., Hsp72 preserves muscle function and slows progression of severe muscular dystrophy, Nature, Apr. 19, 2012, vol. 484, pp. 394-398, Macmillan Publishers Limited.

Binnur Eroglu, et al., Therapeutic Inducers of the HSP70/HSP110 Protect Mice Against Traumatic Brain Injury, Journal of Neurochemistry, Sep. 2014, pp. 626-641, vol. 130, Issue 5.

Jose-Alberto Palma, et al., Current Treatments in Familial Dysautonomia, Expert Opinion on Pharmacotherapy, Dec. 2014, pp. 1-32, vol. 15, Issue 18.

J. Thomas Cribbs, et al., Functional Characterization of Phosphorylation Sites in Dynamin-Related Protein 1, Methods in Enzymology, 2009, pp. 1-21, vol. 457.

Lynn George, et al., Familial dysautonomia model reveals Ikbkap deletion causes apoptosis of Pax3+ progenitors and peripheral neurons, PNAS, Nov. 12, 2013, pp. 18698-18703, vol. 110, No. 46.

Jae-Hyun Kim, et al., Human Elongator facilitates RNA polymerase II transcription through chromatin, PNAS, Feb. 5, 2002, pp. 1241-1246, vol. 99, No. 3.

Dec. 16, 2016, EP search report issued for related EP application No. 16177516.8.

\* cited by examiner

USE OF BGP15 TO TREAT FAMILIAL DYSAUTONOMIA

This invention was made with government support under Contract No. NIH R01 NS035714 and Contract No. NIH R01 NS086796, awarded by the National Institutes of Health. The government has certain rights in the invention.

FIELD OF THE INVENTION

The present invention relates to the use of O-(3-piperidino-2-hydroxy-1-propyl)-nicotinic amidoxime (BGP15), tautomers, enantiomers and pharmaceutically acceptable salts thereof for the treatment of Familial Dysaustonomia

BACKGROUND OF THE INVENTION

Familial Dysautonomia (FD, OMIM #223900) is an hereditary sensory and autonomic neuropathy, mostly affecting persons of Ashkenazi descent. Symptoms vary from patient to patient, and include insensitivity to pain (due to loss of nociceptors and thermoreceptors in the Dorsal Root Ganglia (DRG) unstable blood pressure and body temperature, frequent pneumonia resulting in chronic lung diseases, poor growth, chronic kidney diseases, optic neuropathy leading to progressive visual loss and gait ataxia. FD patients typically can expect a shortened lifespan, and currently have a 50% probability of surviving beyond the age of 40.

The disease is known to be the result of a mutation in the gene inhibitor of kappa B kinase complex-associated protein (IKBKAP, Anderson et al., 2001), which in turn results in tissue-specific reductions of IKAP protein. The exact function of IKAP is not yet fully understood. The protein appears to be required for modification of tRNAs during translation and may function directly or indirectly in the transcription (Hawkes et al., 2002; Karlsborn et al., 2014; Kim et al., 2002).

Current pharmacological treatment of FD is focussed on the management of the various symptoms of the disease (Palma et al., 2014).

There is thus an urgent need to find a treatment of FD that acts at a neuronal level by modulating the effect of the IKAP deficiency which is responsible for the syndrome.

PRIOR ART

The compound of formula I, (I)

O-(3-piperidino-2-hydroxy-1-propyl)-nicotinic amidoxime, also known as BGP15, is mostly known in the art for use in the treatment of diabetes (Literáti-Nagy et al., 2014). WO2013024311 and Gherig et al. (2012) describe the usefulness of BGP15 for treating muscle atrophy. WO2005123049 describes effect of BGP15 on mitochondrial genesis and its possible use in muscle regeneration. WO9713504 describes the use of BGP15 for neurodegenerative disorders, myopathy and various diseases of mitochondrial origin.

Nagy et al. (2010) describe how BGP15 prevents AIF mitochondria to nucleus translocation and mitochondrial depolarisation in liver cells. WO2005123049 discloses that BGP15 can increase the number of mitochondria in various tissues.

BGP15 is also known for the treatment of acquired muscle myopathy and rhabdomyolysis (WO2013003593), traumatic brain injury (Eroglu et al., 2014) and peripheral neuropathy (Bardos et al., 2003).

Studies by Mendoza-Santiesteban et al, (2012, 2014) show in patients with Familial Dysautonomia, the temporal retina is more impaired than is the nasal retina using OCT and histology. This observation is reminiscent of the phenotype observed in two other optic neuropathies, Leber's and DOA, which result from mutations in mitochondrial genes. Based on this observation, they posit that FD may also result from an impairment in mitochondrial function. In a clinical retrospective chart review paper, Palma et al. (2015) report an increased incidence of rhabdomyolysis in FD patients. They posit that this may be due to impairments in mitochondrial function.

DETAILED DESCRIPTION OF THE INVENTION

We have surprisingly found that BGP15 is useful in the treatment of familial dysautonomia. Indeed, we have surpisingly found that mitochondrial function is impaired in neurons of an extremely relevant FD animal model and that the rescue of such impaired function by BGP15 is able to mitigate the effect of the disease at a neuronal level.

Accordingly, there is provided the compound of formula I above, its tautomers, enantiomers or pharmaceutically acceptable salts thereof for use in the treatment of familial dysautonomia.

As set out in the examples below, we have tested BGP15 in cellular and animal models of FD, using the IKBKAP conditional knock-out (CKO) Wnt1-cre:Ikbkap$^{-/-}$ mouse model described in George et al., 2013. This animal model exhibits hallmarks of the disease including activation of programmed cell death of Peripheral Nervous System (PNS) neurons. FD patients have a severe loss of these TrkA+ neurons, which is recapitulated in this particular mouse model of the disease both in vitro and in vivo. We show here that their death can be prevented in vitro and in vivo with application of BGP-15. In addition we show that BGP15 improves mitochondrial function of FD neurons and enhances heart innervation in Ikbkap$^{-/-}$ mice in vivo.

EXAMPLES

Figure 1A:
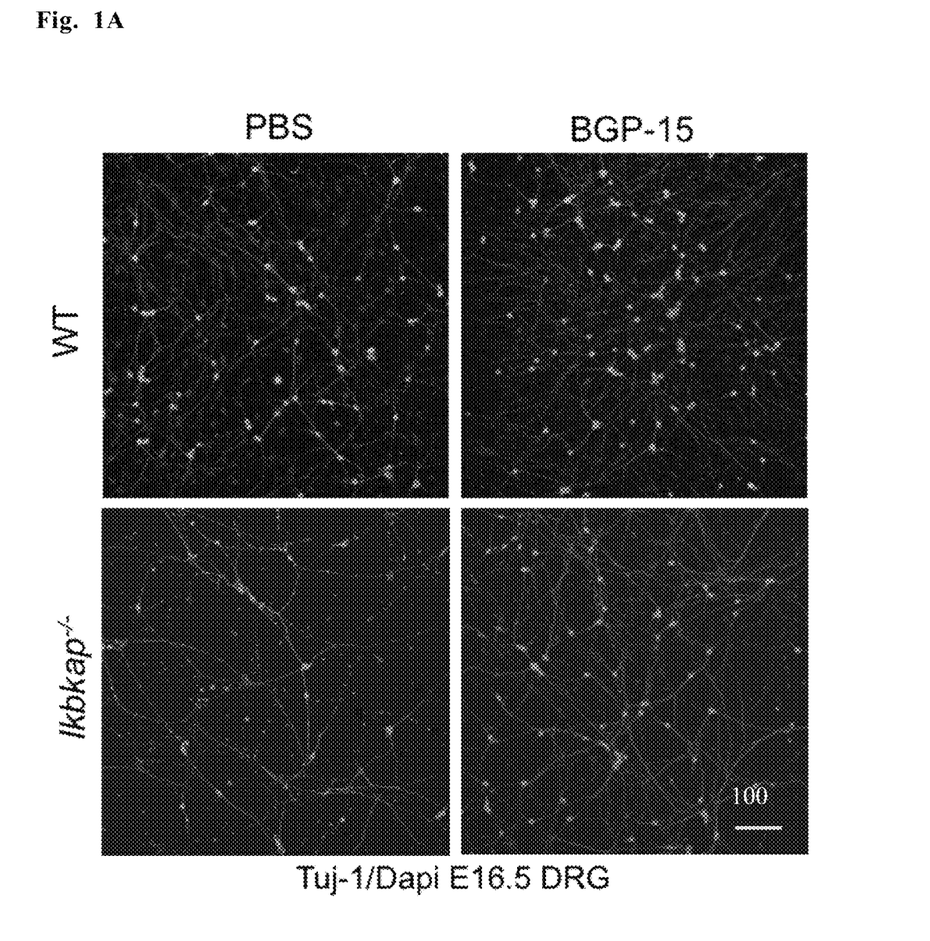
FIG. 1A—Tuj-1 and DAPI imaging of Wild Type (WT) and Ikbkap$^{-/-}$ mice neurons treated or untrated with BGP15
Figure 1B:
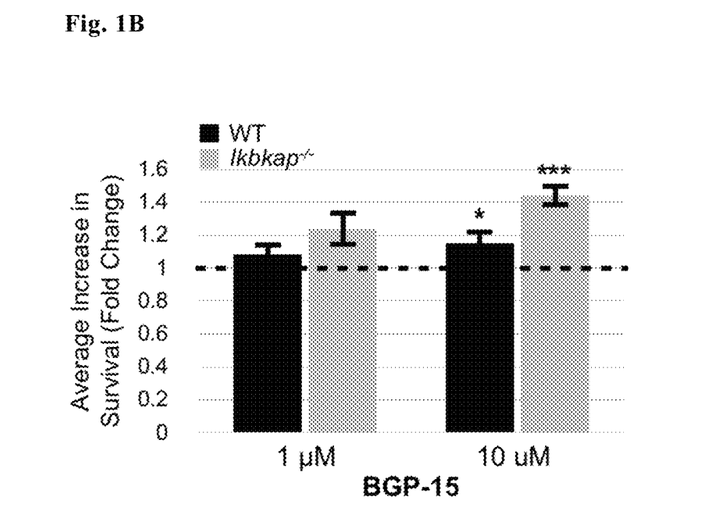
FIG. 1B—Cell counts of WT and Ikbkap$^{-/-}$ mice neurons treated or untrated with BGP15

Example 1—(FIG. 1) Death of Dorsal Root Ganglia Neurons from Ikbkap$^{-/-}$ Embryos is Significantly Decreased by BGP15 Both In Vitro and In Vivo Representative images (FIG. 1A) and cell counts (FIG. 1B, where the dashed line indicates baseline counts from Phosphare Buffer Saline (PBS) treated Ikbkap$^{-/-}$ and WT culture used to determine the fold change of treatments, and where data was acquired from 10 WT and 10 Ikbkap$^{-/-}$ mice) of DRG neurons plus or minus the addition of BGP15 to both E16. 5 Wild Type (WT) and IKBKAP$^{-/-}$ DRG neuronal cultures demonstrate a dramatic improvement upon treatment with 10 μM BGP15.

Figure 1C:
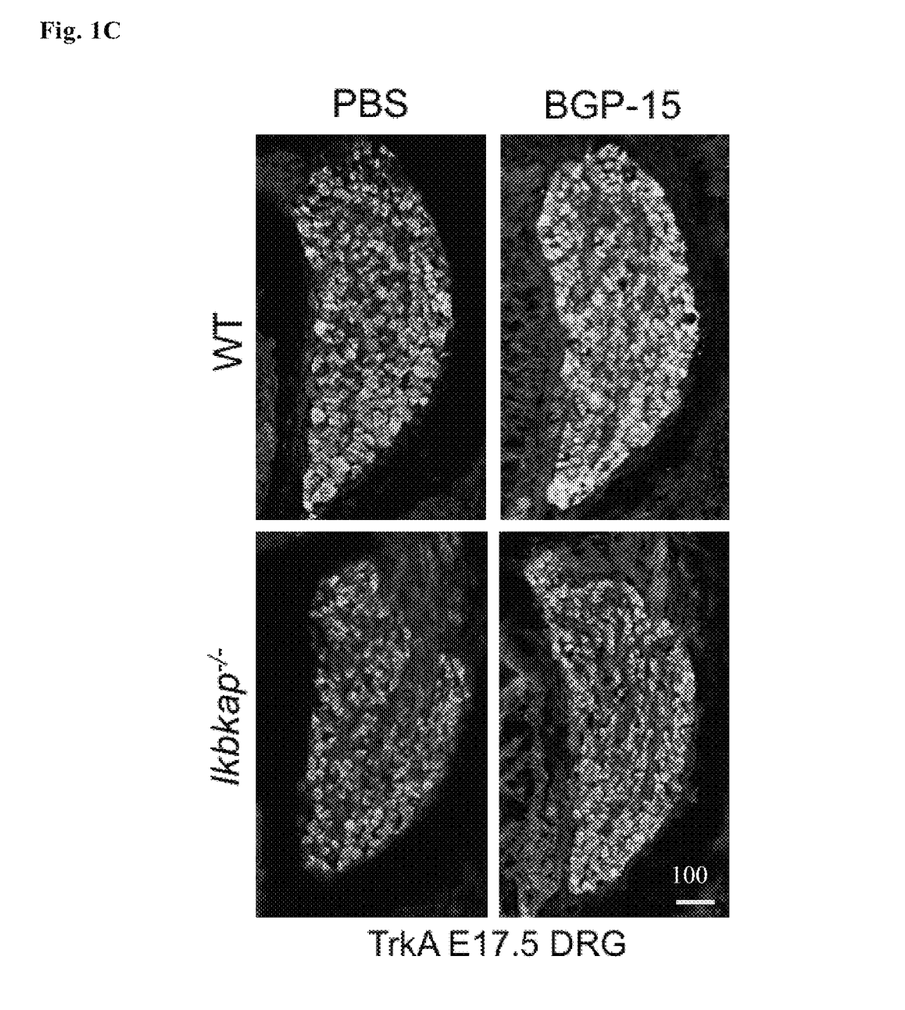
FIG. 1C—TrkA imaging of WT and Ikbkap$^{-/-}$ embryos neurons treated or untrated with BGP15 whilst in utero.
Figure 1D:
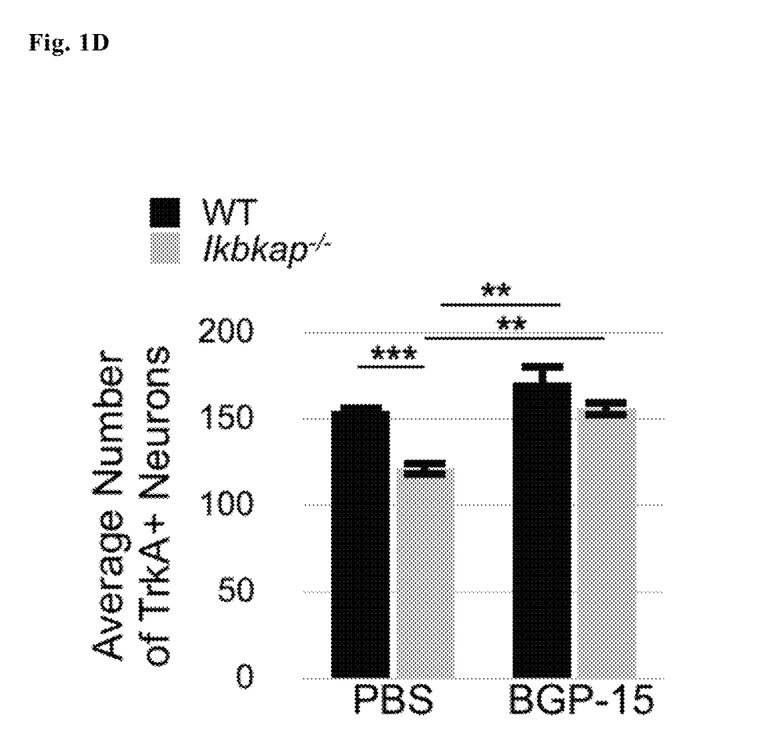
FIG. 1D—Cell counts of WT and Ikbkap$^{-/-}$ embryos neurons treated or untrated with BGP15 whilst in utero.
Figure 2A:
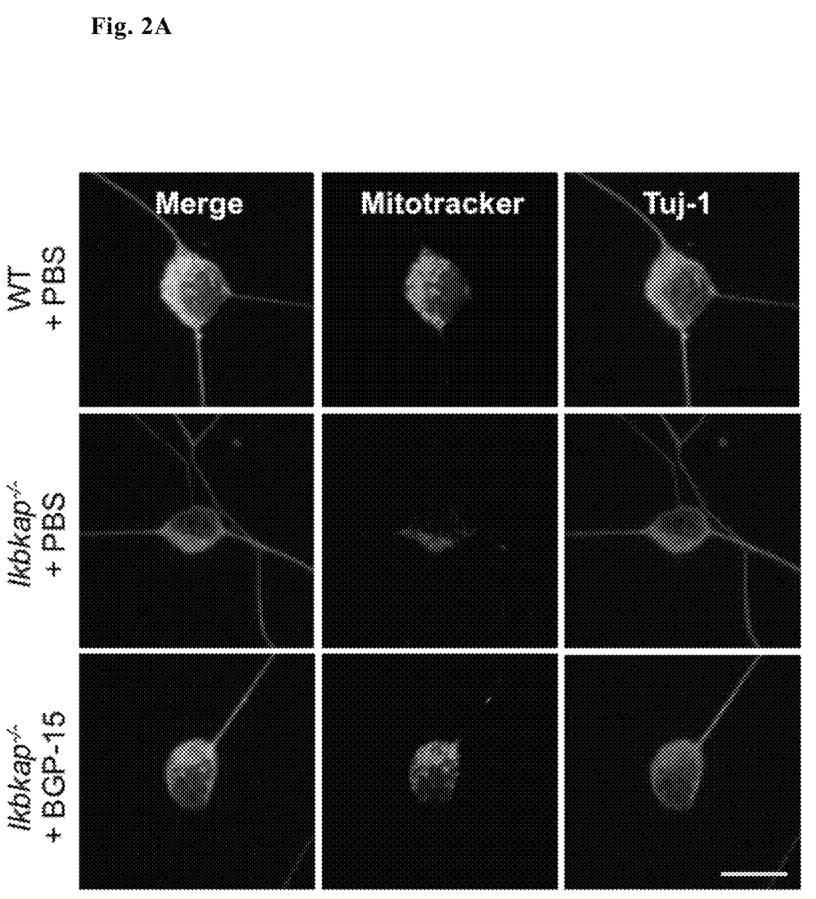
FIG. 2A—Mitotracker and Tuj-1 imaging of WT and Ikbkap$^{-/-}$ embryos neurons treated or untreated with BGP15
Figure 2B:
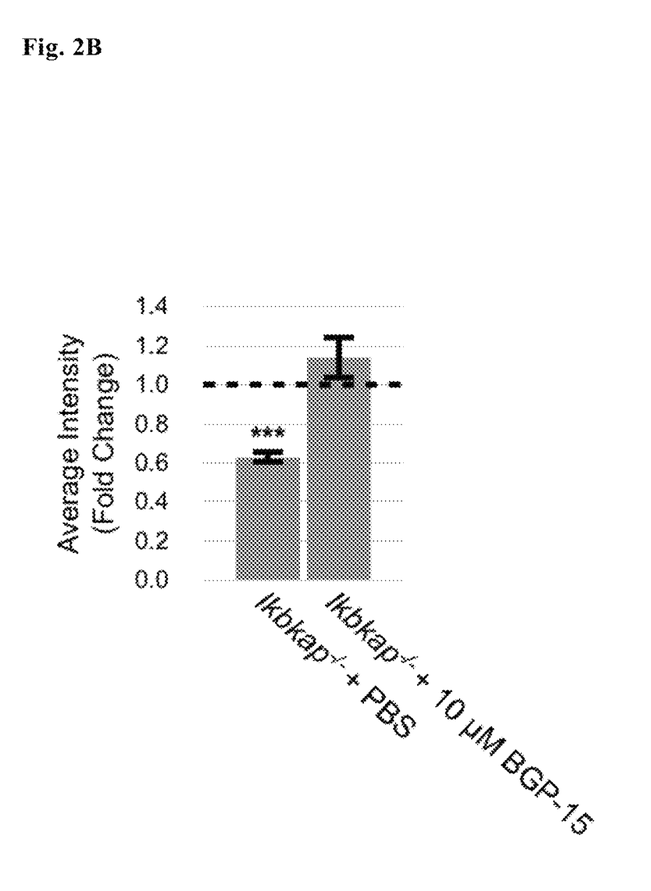
FIG. 2B—Mitotracker cell counts of Ikbkap$^{-/-}$ embryos neurons treated or untreated with BGP15
Figure 2C:
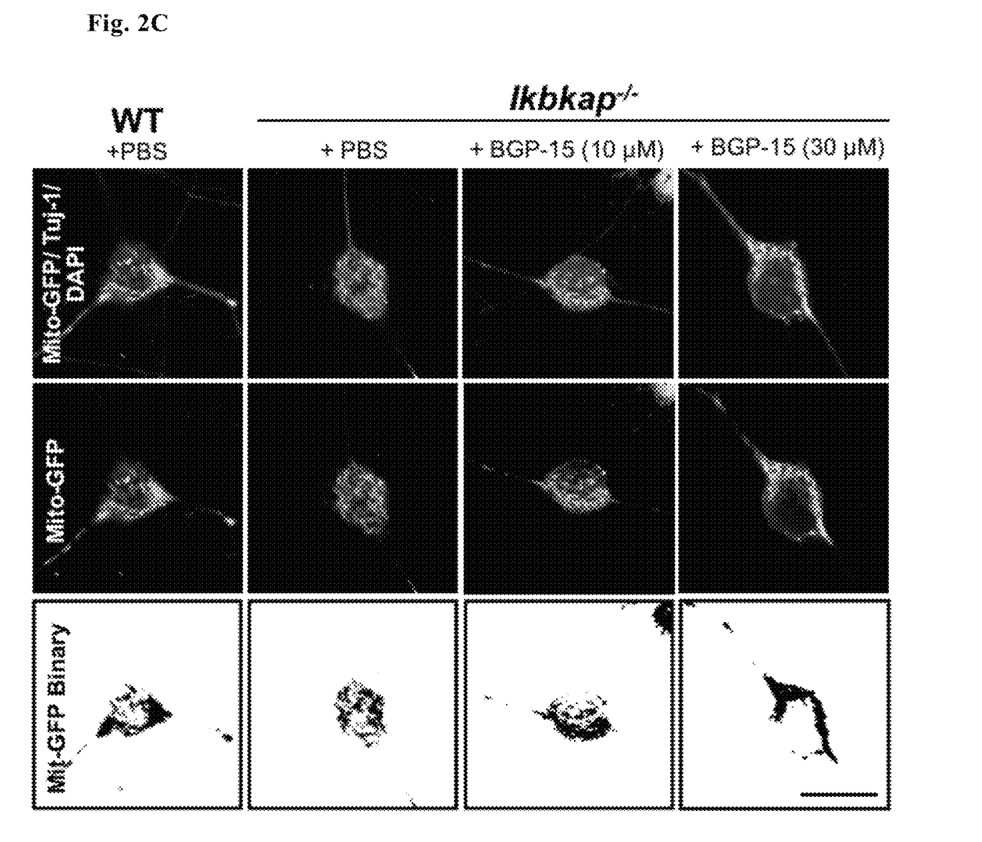
FIG. 2C—Mitotracker, Tuj-1 and DAPI imaging of Wild Type and Ikbkap$^{-/-}$ neurons treated or untreated with BGP15
Figure 2D:
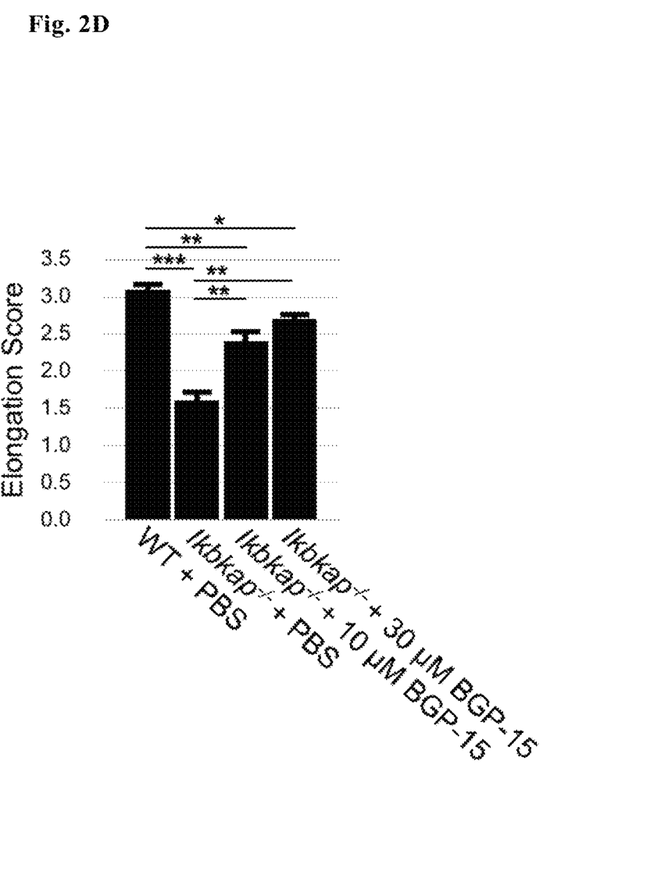
FIG. 2D—Elongation score of WT and Ikbkap$^{-/-}$ neurons treated or untreated with BGP15
Figure 2E:
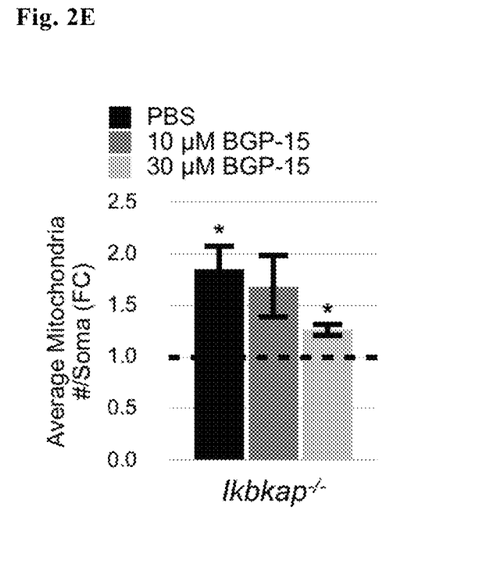
FIG. 2E—Average mitochondrial numbers of Ikbkap$^{-/-}$ neurons treated or untreated with BGP15
Figure 2F:
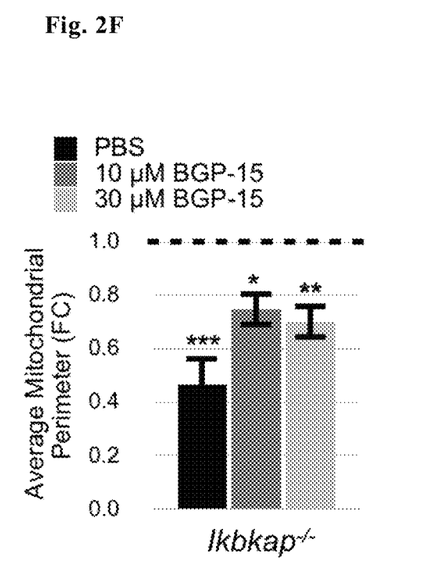
FIG. 2F—Average mitochondrial perimeter of Ikbkap$^{-/-}$ neurons treated or untreated with BGP15
Figure 2G:
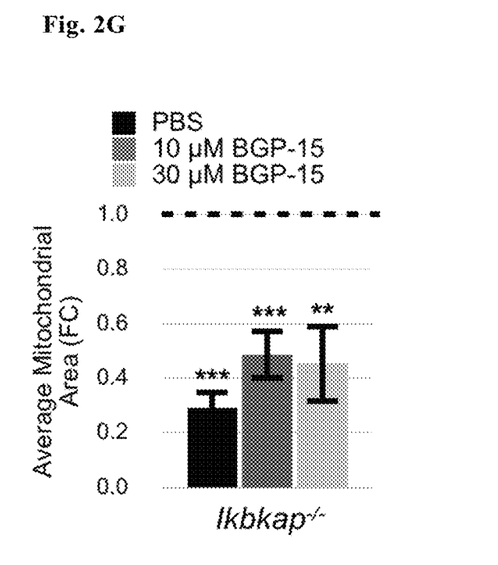
FIG. 2G—Average mitochondrial area of Ikbkap$^{-/-}$ neurons treated or untreated with BGP15

This effect is confirmed in vivo, as set out in FIGS. 1C and 1D where the representative images and cell counts (using TrkA counts) are depicted, respectively, of DRG neurons from both E17.5 Wild Type and and IKBKAP$^{-/-}$ embryos, either treated in utero with daily 100 mg/kg BGP15 or untreated (injected with PBS solution). Data from FIG. 1D represent 4-Ikbkap$^{-/-}$+ saline, 5-Ikbkap$^{-/-}$+BGP-15, 6-WT+ saline, and 5-WT+BGP-15 embryos, respectively.

An antibody to beta III tubulin (tuj-1), a neuron-specific microtubule protein of the cytoskeleton, along with the nuclear stain Dapi were used to identify neural cell bodies for in vitro counts (FIGS. 1A and B), while an antibody to the TrkA receptor was used to identify the small diameter nociceptors and thermoreceptors in vivo (FIGS. 1 C and D)

Example 2—(FIG. 2)—Mitochondrial Dysfunction Observed in Ikbkap$^{-/-}$ DRG Neurons is Rescued by BGP15

Unhealthy, impaired mitochondria are often marked by a decreased membrane potential and disrupted morphology. Two fluorescent probes were used to measure mitochondrial health MitoTracker CMXRos (a dye that accumulates dependent on membrane potential) to measure differences in membrane potential of WT and Ikbkap$^{-/-}$ inner mitochondrial membranes (FIGS. 2A and B) and CellLight Mitochondria-GFP Bacmam 2.0 (a viral delivery system that transports a fluorescently-fused mitochondrial gene independent of mitochondrial membrane potential) to determine mitochondrial morphology (FIG. 2C-G). Mitochondria of Ikbkap$^{-/-}$ small diameter DRG were found to be both depolarized and fragmented. Addition of BGP-15 to the culture media fully stabilized the mitochondrial membrane potential and partially restored the fragmentation that occurred in Ikbkap$^{-/-}$ neurons.

Representative images (FIG. 2A) of WT, Ikbkap$^{-/-}$ and BGP15-treated Ikbkap$^{-/-}$ E17.5 DRG neurons, together with Mitotacker intensity counts (FIG. 2B, where the dotted line show baseline measurements of PBS treated WT mitochondria and where significance represents measurements taken from 145-DRG neurons from 22-WT and 16-Ikbkap$^{-/-}$ embryos from a total of 11 pregnant dams) of the Ikbkap$^{-/-}$ DRG neurons treated with either PBS buffer alone or BGP15 show that BGP15 rescues depolarized mitochondria in Ikbkap$^{-/-}$ DRG neurons to WT levels.

Representative images (FIG. 2C) and elongation score (FIG. 2D) and Image J quantification of mitochondrial number of soma (FIG. 2E), mitochondrial perimeter (FIG. 2D) and mitochondrial area (FIG. 2F) of WT, Ikbkap$^{-/-}$ and BGP15-treated Ikbkap$^{-/-}$ E17.5 DRG neurons (FIG. 2D, where significance represents measurements taken from 595-DRG neurons from 14-WT and 11-Ikbkap$^{-/-}$ embryos from a total of 6 pregnant dams) show that addition of BGP-15 as compared to PBS buffer alone to Ikbkap$^{-/-}$ DRG neuronal cultures also partially restored fragmented mitochondrial networks observed in Ikbkap$^{-/-}$ DRG neurons.

Example 3—(FIG. 3)—Disrupted Sensory and Sympathetic Innervation of Hearts in Ikbkap$^{-/-}$ Embryos is Restored with BGP15

Correct and complete innervation of neuronal targets is necessary for neuronal survival. Ikbkap$^{-/-}$ neuronal axons are stunted and more branched than WT DRG neurons in vitro (preliminary data). To determine whether this phenomenon also occurs in vivo, innervation of the heart by sympathetic and sensory neurons was quantified in embryos that had been exposed in utero to BGP-15 or saline (via intraperitoneal injections into pregnant dams). Axonal branching patterns and degree of innervation (FIG. 3 A-D) was measured. Hearts were dissected from embryos after daily treatment with BGP-15 at E17.5. Axons were identified using the neuronal tuj-1 antibody and extent of innervation quantified in the heart. Our data show that Ikbkap axons fail to fully innervate the heart, compared to their WT littermates: they fail to reach the inferior pole of the heart, and branch less frequently than controls. To our surprise, in utero exposure to BGP-15 but not saline significantly improved heart innervation both in terms of increasing branching and promoting more normal axon elongation towards the inferior heart pole.

Figure 3A:
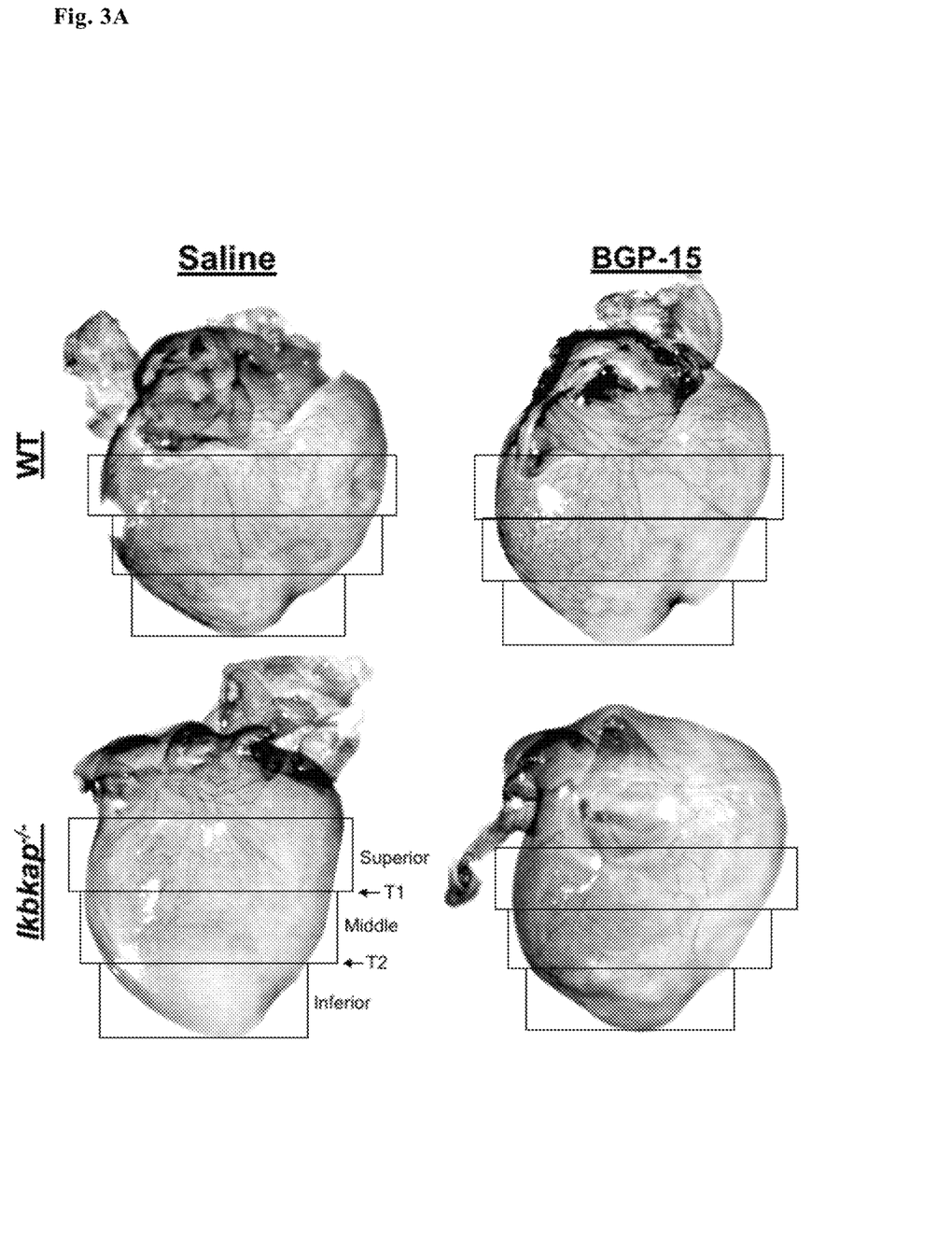
FIG. 3A—Representative images of WT and Ikbkap hearts harvested from E17.5 embryos injected with ether saline or BGP-15 and regions of interest (ROI)

FIG. 3A shows representative images of both WT and Ikbkap hearts harvested from E17.5 embryos treated in utero with ether saline or BGP-15. Five regions of interest (ROI) were used to quantify degree and patterning of innervation: Superior, Middle and Infererior, as well and two transition zones between these regions: Transition 1 (T1) and Transition 2 (T2)

Figure 3B:
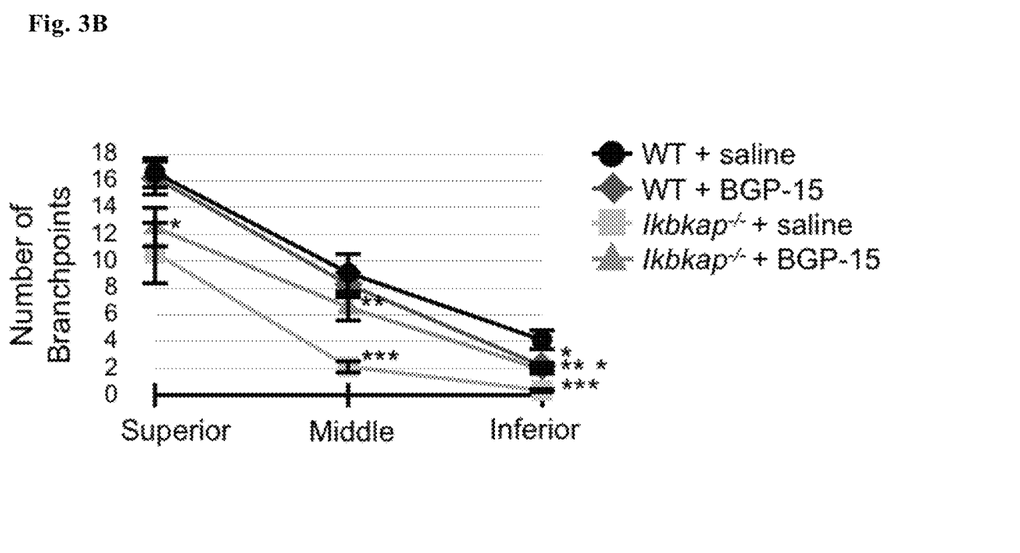
FIG. 3B—Number of branchpoints in three different ROIs of WT and Ikbkap$^{-/-}$ hearts treated or untreated with BGP15
Figure 3C:
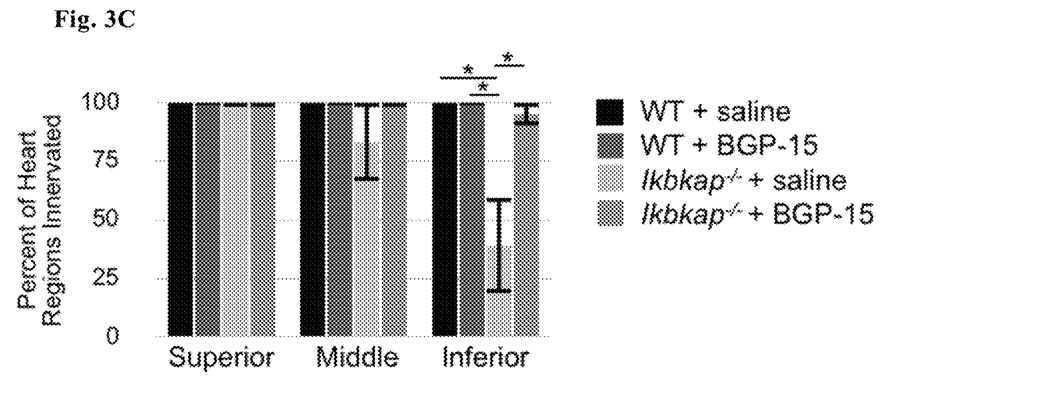
FIG. 3C—Percentage of innervation in three different ROIs of WT and Ikbkap$^{-/-}$ hearts treated or untreated with BGP15

FIG. 3B. shows quantification of branch points in 3 ROIs, depending on treatment used FIG. 3C shows the percentage of percent of in 2 ROIs of each treatment with axons present.

Figure 3D:
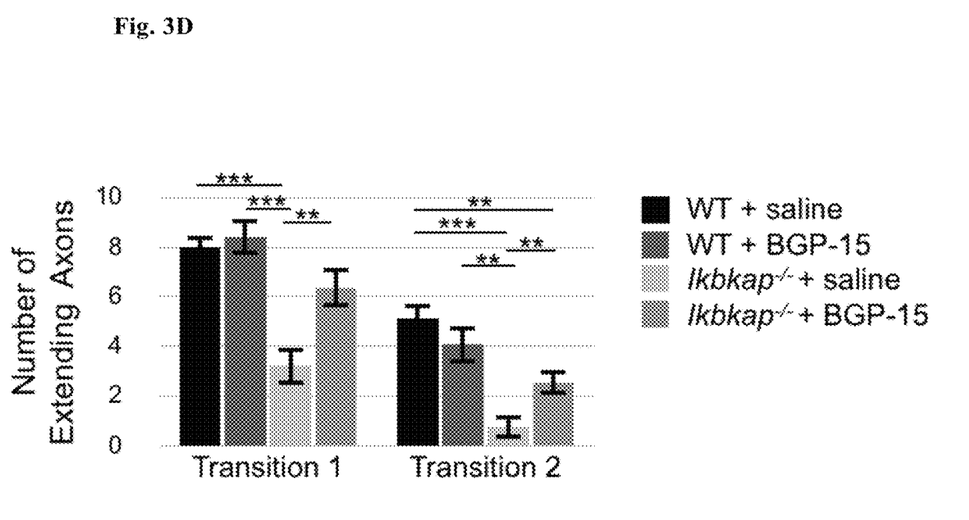
FIG. 3D—Number of axons in two different ROIs of WT and Ikbkap$^{-/-}$ hearts treated or untreated with BGP15

FIG. 3D shows number of extending axons across Transition 1 and Transition 2, depending on the treatment used.

Significance in FIGS. 3B-D represents 10-WT saline, 10-Ikbkap$^{-/-}$ saline, 11-Ikbkap$^{-/-}$ BGP-15, and 12-WT BGP-15 injected hearts from 12 pregnant dams Materials and Methods Genetically Modified Mice.

To understand the disrupted events that occur in selected neuronal subpopulation of the PNS in FD patients, the Ikbkap$^{-/-}$ gene was conditionally deleted from the neural crest cell lineage using a Wnt1-Cre transgene as previously described (George et al., 2013).

Immunostaining.

Both cell culture and sectioned tissue were labeled as previously described (Rifkin et al., 2000). Primary antibodies included tuj-1 (Covance, 1:1000), trkA (gifted from Dr. Louis Reichardts of UCSF, 1:5000), and anti-GFP (ThermoFisher, 1:2000). Secondary antibodies and stains included Alexa 488 and 568 (ThermoFisher, 1:2000) along with Dapi (ThermoFisher, 1:3000). Wells and slides were imaged using a Leica TCS SP8 confocal microscope using Leica Application Suite Advanced Fluorescence 3.3.0.10134 software. Whole mount heart imaging using diaminobenzidine (DAB) immunohistochemistry was performed as previously described (Enomoto et al., 2001) using the primary antibody tuj-1 (1:1000), secondary-linked horseradish peroxidase goat anti mouse-HRP (SouthernBiotech, 1:500), and the DAB-Plus reagent kit (ThermoFisher) for development. Hearts were imaged using a Zeiss Stemi SV11 APO stereo microscope and ProGress Mac Capture Pro software.

In Vivo Survival Assays.

Pregnant dams were injected with either PBS or 100 mg/kg BGP-15 (gifted from Dr. Mike Brownstein) from E12.5 to E16.5. Embryos were sacrificed at E17.5, genotyped, and frozen as previously described (Rifkin et al., 2000). Tissue was cryosectioned at 16 μm using a Lecia CM 1950 cryostat, and sections of the upper lumbar region were stained with anti-TrkA for cell counts. Data represent average count of trkA+ cells of the DRG±SEM. Significance was determined using the one-way ANOVA and student t-test.

Primary Culture of Mouse DRG Neurons.

DRG were dissected from E16.5 and E17.5 embryos. Embryos were genotyped and DRG from either WT or Ikbkap$^{-/-}$ pups were pooled and stored overnight at 4° C. in Hibernate-E media (ThermoFisher) supplemented with 2% B-27 (Gibco) and 1×L-glutamine (Gibco). Nunc LabTek II chambered coverglass 8 well slides (Sigma) were coated with 10 μg/mL poly-d-lysine (Millipore) and 10 μg/mL laminin (ThermoFisher). To dissociate neurons for plating, DRG were incubated with 0.05% trypsin+EDTA (ThermoFisher) at 37° C. for 16 minutes. Trypsin was quenched with 10% FBS (ThermoFisher) in Neurobasal. DRG neurons were resuspended in a supplemented Neurobasal media consisting of 2% B-27, 100 μg/ml penicillin/streptomycin (Mediatech), 1×L-glutamine, and 25 ng/mL NGF (gifted from Dr. Thomas Large). Approximately 400 μl of supplemented Neurobasal media per embryo dissected was added for resuspension. Cells were dissociated with a series of fire-pulled pasteur pipettes, and the cell solution was passed through a 40 μM Falcon Cell Strainer (Fisher Scientific) to eliminate any remaining clumps for plating equal numbers. Cells were counted with a hemocytometer and plated at final cell density of $2.0\times10^4$ cells/well and incubated at 37° C., 5% $CO_2$ for up to 72 hours.

In Vitro Survival Assay.

Either PBS or BGP-15 (1, 10 μM) was added to E16.5 DRG neurons at the time of plating in supplemented Neurobasal media. Equal numbers of neurons were plated per well. Cells were incubated for 40 hours at 37° C., 5% $CO_2$ and fixed as stated previously. Cells were stained with Dapi and Tuj-1 and the number of neurons in the entire well was quantified. Survival increase/decrease was determined from baseline PBS-treated WT counts. BootstRatio analysis (Cleries et al., 2012) was used to determine significance of the fold increase found from each experiment (n=5).

Mitochondrial Assays.

To measure mitochondrial membrane potential, BGP-15 (10 μM) or saline treated E17.5 WT and Ikbkap$^{-/-}$ DRG neurons (18 hours at 37° C. and 5% $CO_2$) were incubated with MitotrackerCMX Ros according to manufacturer's instruction (ThermoFisher). Conditions of the incubation were optimized at 200 nM of Mitotracker CMX Ros for 25 minutes at 37° C., 5% $CO_2$. Neurons were fixed as stated previously, stained with tuj-1 and Dapi, and imaged using a 63× objective. All imaging parameters were held constant for each experiment for accurate comparison between WT and Ikbkap$^{-/-}$ retention of the Mitotracker dye. Intensity measurements were taken at 568 excitation of somata, throughout the well. BootstRatio was used to calculate significance of the intensity fold decrease determined from data normalized to the PBS-treated WT average intensity of each experiment (n=9).

To measure mitochondrial morphology, 8 uL of CellLight Mitochondria-GFP, BacMam 2.0 (ThermoFisher) was added according to the manufacturer's protocol to wells of WT and Ikbkap$^{-/-}$ DRG neurons at the time of plating along with BGP-15 (10 uM or 30 uM) or PBS treatment. Optimized delivery of the CellLight Mitochondria-GFP was found at 40 PPC and a total incubation time of 45 hours. Cells were fixed as described previously. Neurons were stained with anti-GFP, tuj-1, and Dapi and imaged using a 63× objective. Morphology was calculated using both ImageJ parameters via the "Analyze Particles" function (Cribbs and Strack, 2009) along with an assigned score of elongation based on selected reference images (Dagda et al., 2008). Mitochondria were scored after randomization of images and blinding of the investigator to the cell type and treatment condition. Significance of the elongation score was calculated using the student t-test, while the BootstRatio analysis was used to determine significance of fold increase of data normalized to PBS-treated WT mitochondria.

Heart Innervation Assay.

Pregnant dams were injected with ether PBS or 100 mg/kg BGP-15 from developmental stage E12.5 to E16.5 and pups were sacrificed at E17.5. Hearts were dissected, genotyped, fixed, and stained for whole mount diaminobenzidine (DAB) immunohistochmesirty as previously described (Enomoto et al., 2001). Hearts were imaged at 10×. The aorta and apex served as upper and lower boundaries for the 3 regions of interest used for quantification. Significance was calculated using the one-way ANOVA and student t-test.

Formulation and Administration

BGP15 is formulated preferably in admixture with a pharmaceutically acceptable carrier, excipient or the like. In general, it is preferable to administer the pharmaceutical composition in orally-administrable form, but certain formulations may be administered via a parenteral, intravenous, intramuscular, transdermal, buccal, subcutaneous, suppository, nasal or other route. One of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients. In certain pharmaceutical dosage forms, the pro-drug form of the compounds, especially including ester and ether derivatives, as well as various salt forms of the present compounds, are preferred. One of ordinary skill in the art will recognize how to readily modify the present compounds to pro-drug forms to facilitate delivery of active compounds to a targeted site within the host organism or patient. The routineer also will take advantage of favourable pharmacokinetic parameters of the pro-drug forms, where applicable, in delivering the present compounds to a targeted site within the host organism or patient to maximize the intended effect of the compound. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount effective to alleviate the symptoms of the subject being treated. While human dosage levels have yet to be optimized for the compounds of the invention, generally, a daily dose is from about 0.05 mg/kg to about 100 mg/kg of body weight. The amount of active compound administered will, of course, be dependent on the subject and disease state being treated, the severity of the affliction, the manner and schedule of administration and the judgment of the prescribing physician. For purposes of the present invention, a prophylactically or preventive effective amount of the compositions according to the present invention (i.e., an amount which substantially reduces the risk that a patient will either succumb to a disease state or condition or that the disease state or condition will worsen) falls within the same concentration range as set forth above for therapeutically effective amounts and is usually the same as a therapeutically effective amount. In some embodiments of the present invention BGP15 is administered in combination with one or more other pharmaceutically active agents. The phrase "in combination", as used herein, refers to agents that are simultaneously administered to a subject. It will be appreciated that two or more agents are considered to be administered "in combination" whenever a subject is simultaneously exposed to both (or more) of the agents. Each of the two or more agents may be administered according to a different schedule; it is not required that individual doses of different agents be administered at the same time, or in the same composition. Rather, so long as both (or more) agents remain in the subject's body, they are considered to be administered "in combination".

REFERENCES

Anderson S L et al., Am J Hum Genet. 2001 March; 68(3):753-8
Bardos G et al., Toxicology and Applied Pharmacology (2003), 190(1), 9-16
Clérier R et al., Comput Biol Med. 2012; 42(4)438-45.
Cribbs and Strack, Methods Enzymol. 2009; 457:231-253.
Dagda et al., J Biol Chem. 2009; 284(20):13843-55.
Enomoto et al., Toxicol. Sci. 2001; 59(1)169-177.
Eroglu B et al., Journal of Neurochemistry (2014), 130(5), 626-641
Gehrig S M et al., Nature (London) 484(7394), 394-398
George L et al., Proc Natl Acad Sci USA. 2013 Nov. 12; 110(46):18698-703
Hawkes N A et al. I Biol Chem. 2002; 277(4):3047-52.
Karlsborn, T et al., RNA Biol. 2014; 11(12):1519-28.
Kim J H et al., *Proc Natl Acad Sci USA*. 2002; 99(3):1241-6.
Literáti-Nagy B et al., Metabolic Syndrome and Related Disorders (2014), 12(2)
Nagy et al., Toxicology and Applied Pharmacology 243. 96-103 (2010)
Palma J A et al., Expert Opin Pharmacother. 2014 December; 15(18):2653-71
Rifkin J T et al., Dev Biol. 2000; 227(2):465-80.

The invention claimed is:

1. A method of treating familial dysautonomia in a subject,
the method comprising administering to the subject an effective amount of the compound of formula I (I)

or pharmaceutically acceptable salts thereof.

* * * * *